(12) United States Patent
Stupp et al.

(10) Patent No.: US 8,772,228 B2
(45) Date of Patent: Jul. 8, 2014

(54) ALIGNED NANOFIBERS AND RELATED METHODS OF USE

(75) Inventors: Samuel I. Stupp, Chicago, IL (US); Shuming Zhang, Evanston, IL (US); Alvaro Mata, Barcelona (ES); Megan A Greenfield, Evanston, IL (US)

(73) Assignee: Northwestern University, Evanston, IL (US)

( * ) Notice: Subject to any disclaimer, the term of this patent is extended or adjusted under 35 U.S.C. 154(b) by 562 days.

(21) Appl. No.: 12/031,250

(22) Filed: Feb. 14, 2008

(65) Prior Publication Data

US 2008/0299657 A1    Dec. 4, 2008

Related U.S. Application Data

(60) Provisional application No. 60/901,611, filed on Feb. 14, 2007.

(51) Int. Cl.
| | | |
|---|---|---|
| *A61K 38/10* | (2006.01) | |
| *A61K 38/00* | (2006.01) | |
| *C07K 7/02* | (2006.01) | |
| *C07K 19/00* | (2006.01) | |

(52) U.S. Cl.
USPC ........... 514/3.2; 514/21.4; 530/300; 977/703; 977/717; 264/1.28

(58) Field of Classification Search
None
See application file for complete search history.

(56) References Cited

U.S. PATENT DOCUMENTS

| | | | | |
|---|---|---|---|---|
| 7,371,719 B2 * | 5/2008 | Stupp et al. | ................ | 424/185.1 |
| 7,452,679 B2 * | 11/2008 | Stupp et al. | .................... | 435/7.1 |
| 7,491,690 B2 * | 2/2009 | Stupp et al. | .................... | 514/1.1 |
| 7,534,761 B1 * | 5/2009 | Stupp et al. | .................... | 514/1.1 |
| 2004/0018961 A1 * | 1/2004 | Stupp et al. | ....................... | 514/7 |

OTHER PUBLICATIONS

Li, et al., 2004, Adv. Mater., 16, 361-366.*
Niece, 2003, J. Am. Chem. Soc., 125, 7146-7147.*
Guler, 2006, Biomacromolecules, 7, 1855-1863.*
Jiang, 2007, Soft Matter, 3, 454-462.*
Silva, 2004, Science, 303, 1352-1355.*
Behanna, 2005, J. Am. Chem. Soc., 127, 1193-1200.*
Matsui, 2001, Langmuir, 17, 7918-7922.*
Hartgerink, 2002, PNAS, 99, 5133-5138.*
Beniash, E. et al., "Self-assembling peptide amphiphile nanofiber matrices for cell entrapment" 2005 Acta Biomaterialia 1(4):387-97.
Engler, A.J. et al., "Matrix elasticity directs stem cell lineage specification" 2006 Cell 126(4):677-89.
Hartgerink, J.D. et al., "Self-Assembly and Mineralization Peptide-Amphiphile Nanofibers" 2001 Science 294 (5547):1684-1688.
Hartgerink, J.D. et al., "Peptide-amphiphile nanofibers: A versatile scaffold for the preparation of self-assembling materials" 2002 PNAS 99(8): 5133-8.
Israelachvili, J.N. et al., Journal of the Chemical Society-Faraday Transactions II, 1976.72:1525-1568.
Kim, C.A. and Berg, J.M., "Thermodynamic beta-sheet propensities measured using a zinc-finger host peptide" 1993 Nature 362(6417)267-270.
Silva, G.A. et al., "Selective Differentiation of Neural Progenitor Cells by High—Epitope Density Nanofibers" 2004 Science 303(5662):1352-5.
Tranquillo, R.T., "Self-organization of tissue-equivalents: the nature and role of contact guidance" 1999 Biochem Soc Symp. (65):27-42.
Veis, A., Sabsay, B., and Chou B.W., Abstracts of Papers of the American Chemical Society. 1989.197:92-Iaec.
Xu, C.Y. et al. "Aligned biodegradable nanofibrous structure: a potential scaffold for blood vessel engineering" 2004 Biomaterials 25(5):877-86.
Yamada, K.M., "Adhesive recognition sequences" 1991 Journal of Biological Chemistry 266(20):12809-12.
Yang, F.et al., "Electrospinning of nano/micro scale poly(L-lactic acid) aligned fibers and their potential in neural tissue engineering" 2005 Biomaterials 26(15):2603-10.

* cited by examiner

*Primary Examiner* — Satyanarayana R Gudibande
(74) *Attorney, Agent, or Firm* — Casimir Jones, S.C.

(57) ABSTRACT

The present invention relates to nanofibers. In particular, the present invention provides aligned nanofiber bundle assemblies. In some embodiments, the aligned nanofiber bundle assemblies are used for tissue regeneration, controlled growth of cells, and related methods (e.g., diagnostic methods, research methods, drug screening).

8 Claims, 19 Drawing Sheets

A:

B:

ALIGNED NANOFIBERS AND RELATED METHODS OF USE

This application claims priority to U.S. Provisional Patent Application Ser. No. 60/901,611, filed Feb. 14, 2007, which is herein incorporated by reference in its entirety.

This invention was made with government support under RO1 DE015920-02 awarded by the National Institutes of Health. The government has certain rights in the invention.

FIELD OF THE INVENTION

The present invention relates to nanofibers. In particular, the present invention provides aligned nanofiber bundle assemblies. In some embodiments, the aligned nanofiber bundle assemblies are used for tissue regeneration, and related methods (e.g., diagnostic methods, research methods, drug screening).

BACKGROUND

Controlled cellular orientation and outgrowth is commonly seen in natural tissues and is closely related to tissue function. For example, in arteries, smooth muscle cells (SMCs) and collagen fibrils are circumferentially oriented at the medial layer to provide mechanical support against circulatory blood pressure (see, e.g., Nerem, R. M. and D. Seliktar, Annual Review of Biomedical Engineering, 2001. 3: p. 225-243; Vaz, C. M., et al., Acta Biomaterialia, 2005. 1(5): p. 575-582). In the adult myocardium, cardiomyocytes elongate and orient in parallel to form a syncytium, which enables propagation of electrical signals (see, e.g., Eschenhagen, T. and W. H. Zimmermann, Circulation Research, 2005. 97(12): p. 1220-1231). Enamel, which provides superb mechanical properties to teeth, is formed by highly aligned ameloblasts producing hydroxyapatite crystals in an ordered manner (see, e.g., Nishikawa, S., Anatomical Record, 1992. 232(4): p. 466-478). The successful formation of neural circuits in vitro and nerve regeneration in vivo also depends on guiding neuronal growth cones along specific pathways to help them find correct targets (see, e.g., Dickson, B. J., Science, 2002. 298(5600): p. 1959-1964). Reproducing these "in-vivo-like" orientation and organization of the cells in an engineering system therefore is a very intriguing and challenging subject.

The established "contact guidance" theory illustrates that in many cases cell or cell process has bi-directional response to anisotropic chemical, structural and/or mechanical property of the substratum (see, e.g., Bellairs R, C. A., Dunn G, Cell behavior. Cambridge: Cambridge University Press, 1982: p. 247-280; Tranquillo, R. T., Biochem Soc Symp, 1999. 65: p. 27-42). Based on this theory, researchers have successfully used techniques such as electro-spinning (see, e.g., Xu, C. Y., et al., Biomaterials, 2004. 25(5): p. 877-86; Yang, F., et al., Biomaterials, 2005. 26(15): p. 2603-2610), laser nanotopography (see, e.g., Zhu, B., et al., Biomaterials, 2004. 25(18): p. 4215-23), micro-contact printing (see, e.g., Schmalenberg, K. E. and K. E. Uhrich, Biomaterials, 2005. 26(12): p. 1423-30; Wang, D. Y., et al., J Biomed Mater Res B Appl Biomater, 2007. 80(2): p. 447-53), microfabrication and mircromachining (see, e.g., Lee, P., et al., Biomed Microdevices, 2006. 8(1): p. 35-41; Mata, A., et al., Biomedical Microdevices, 2002. 4(4): p. 267-275; Charest, J. L., A. J. Garcia, and W. P. King, Biomaterials, 2007. 28(13): p. 2202-10) to create patterned substrates and demonstrated the capability to orient cells in monolayer tissue culture. However, tissue engineering (TE) scaffolds are structurally distinct in that they are three-dimensional (3-D). It is thus more attractive to realize alignment of cells in a 3-D environment. Some earlier researchers achieved this by using dynamic culture conditions (see, e.g., Kanda, K. and T. Matsuda, Cell Transplant, 1994. 3(6): p. 481-92) and gradient chemotropic guidance (see, e.g., Tessierlavigne, M., et al., Nature, 1988. 336 (6201): p. 775-778). More recently, researchers developed photo labile hydrogels, and used light to guide cell growth (see, e.g., Luo, Y. and M. S. Shoichet, Nature Materials, 2004. 3(4): p. 249-253). However, a more general and simpler method is still preferred in order to fabricate sophisticated engineering devices.

Improved methods for generating and using aligned nanofiber bundle assemblies are needed.

SUMMARY

The present invention relates to nanofibers. In particular, the present invention provides aligned nanofiber bundle assemblies. In some embodiments, the aligned nanofiber bundle assemblies are used for tissue regeneration, and related methods (e.g., diagnostic methods, research methods, drug screening).

Peptide amphiphiles molecularly designed to aggregate into β-sheet structures are known to self-assemble into cylindrical nanofibers. These nanofibers can be functionalized with epitopes and have shown great potential for use in regenerative medicine and drug delivery systems. A challenge in these systems is to gain control over the length and macroscopic alignment of the nanofibers in order to create structures that can spatially guide cells and control their behavior including migration, proliferation and differentiation. In experiments conducted during the course of developing embodiments for the present invention, methods for creating synthetic analogues (e.g., synthetic extracellular matrix (ECM) analogues) composed of extremely long and aligned nanofibers from self-assembling peptide amphiphile molecules were developed. The ability of such systems to align cells within oriented matrices was exemplified with human mesenchymal stem cells (hMSCs), human bladder smooth muscle cells (bSMCs) and primary dorsal root ganglion (DRG) cells. Such matrices were shown to be versatile in chemical compositions, mechanical properties and orientation factor, and can be applied in many biomedical systems.

In certain embodiments, the present invention provides compositions comprising aligned nanofibers comprising self-assembling peptide amphiphile molecules. The present invention is not limited to particular self-assembling peptide amphiphile molecules (see e.g., Hartgerink, J. D., et al., PNAS USA, 2002. 99(8): p. 5133-8). In some embodiments, the molecules comprise a hydrophobic tail, a peptide segment configured for β-sheet formation, and a segment (e.g., a peptide segment) comprising a net positive or negative charge. In some embodiments, the self-assembling peptide amphiphile molecules interact to form aligned nanofibers.

The self-assembling peptide amphiphile molecules are not limited to a particular type of hydrophobic tail. In some embodiments, the hydrophobic tail comprises an alkyl tail having approximately 16 (e.g., 12, 13, 14, 15, 16, 17, 18, 19, 20, 30, 50, 100) carbon atoms that may be linear or branched, saturated or unsaturated. In some embodiments, the alkyl tail is derivatized with, for example, halogens, radiolabeled atoms, or other desired molecules. The self-assembling peptide amphiphile molecules are not limited to a particular type of peptide segment configured for β-sheet formation. In some embodiments, the peptide segment configured for β-sheet formation comprises uncharged amino acid residues (e.g., alanine, glycine, isoleucine, leucine, methionine, phenylalanine, proline, tryptophan, and/or valine). In some embodiments, the peptide segment configured for β-sheet formation comprises three alanine and three valine amino acid residues.

The self-assembling peptide amphiphile molecules are not limited to a particular type of charged segment. In some embodiments, the charged segment comprise a charged peptide segment. In some embodiments, the charged peptide segment has a positive charge. In some embodiments, the charged peptide segment has a negative charge. In some embodiments, the charged peptide segment comprises charged amino acid residues (e.g., positively charged amino acids such as aspartic acid and glutamic acid) (e.g., negatively charged amino acids such as arginine, histidine, and lysine). In some embodiments, the charged peptide segment comprises three glutamic acid residues. In some embodiments, the charged peptide segment comprises metal chelators. In some embodiments, the charged peptide segment increases the solubility of the self-assembling amphiphile molecules.

The aligned nanofibers are not limited to a particular formation. In some embodiments, the formation of the aligned nanofibers is a noodle-like formation. In some embodiments, the formation of the aligned nanofibers is a bubble-like formation.

In certain embodiments, the present invention provides methods for forming aligned nanofibers. The present invention is not limited to particular methods for forming aligned nanofibers. In some embodiments, the methods comprise heating self-assembling peptide amphiphile molecules from approximately 25° C. to approximately 80° C., and cooling the self-assembling peptide amphiphile molecules to approximately 25° C.

In certain embodiments, the present invention provides methods for directing cellular growth orientation along a nanofiber. The present invention is not limited to particular methods for directing cellular growth orientation along a nanofiber. In some embodiments, the methods comprise combining living cells (e.g., stem cells) (e.g., human mesenchymal stem cells (hMSCs), human bladder smooth muscle cells (bSMCs) and primary dorsal root ganglion (DRG) cells) with self-assembling peptide amphiphile molecules described above. In some embodiments, the methods result in the living cells growing in an orientation consistent with the direction of the aligned nanofibers. In some embodiments, the cells are implanted into a living subject (e.g., for purposes of treating a disease, for purposes of tissue regeneration, or for research or drug screening applications).

DETAILED DESCRIPTION

Figure 1:
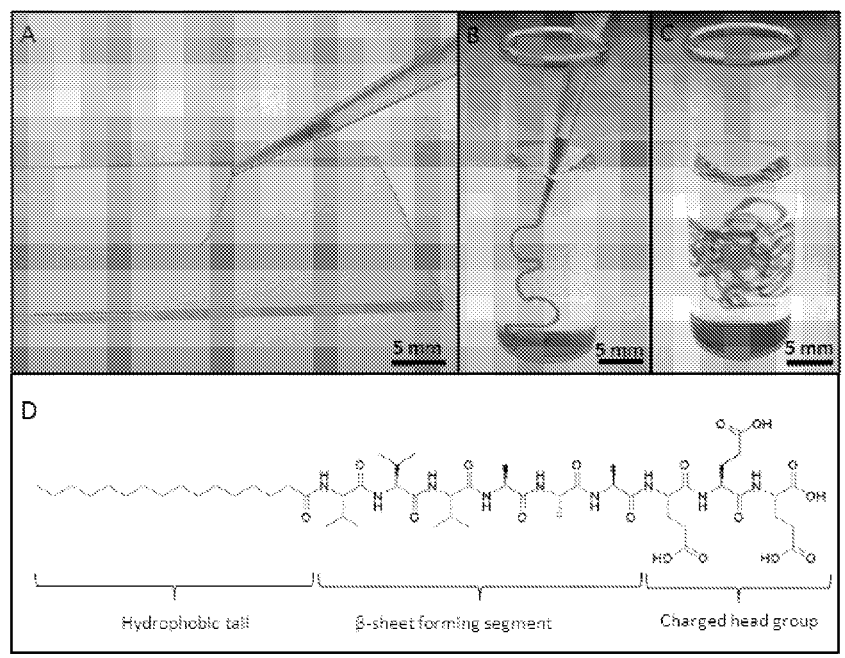
FIG. 1 shows a 2 wt % Noodle structure (A) gelling on glass slide, (B) forming in glass vials (C) being stored in glass vials. Noodle in (A-C) were stained with trypan blue for better visualization. (D) A typical self-assembly peptide amphiphile molecule, which is composed of hydrophobic arkyl tail, β-sheet forming segment (peptide sequence VVVAAA, SEQ ID NO.:14) and charged head group (peptide sequence EEE).

Inspired largely by biological systems, molecular self-assembly continues to be a theme of great interest. Research efforts in self-assembly cover a broad spectrum ranging from the possibility of accessing materials or devices with minimal machine intervention (see, e.g., Whitesides, G. M., et al., Science, 1991. 254(5036): p. 1312-1319; Reches, M. and E. Gazit, Science, 2003. 300(5619): p. 625-627; Stoykovich, M. P., et al., Science, 2005. 308(5727): p. 1442-1446) to the understanding of fibril self-assembly among misfolded proteins in disease (see, e.g., Gazit, E., Faseb Journal, 2002. 16(1): p. 77-83; Jimenez, J. L., et al., Embo Journal, 1999. 18(4): p. 815-821; Petkova, A. T., et al., Science, 2005. 307 (5707): p. 262-265). The ability to predict the crystal structure of supramolecular aggregates with less order than perfectly periodic crystals is in its very early stages. However, there have been important achievements over the past few decades in crystal engineering (see, e.g., Russell, V. A., et al., Science, 1997. 276(5312): p. 575-579; Lehn, J. M., Angewandte Chemie-International Edition in English, 1990. 29(11): p. 1304-1319; Moulton, B. and M. J. Zaworotko, Chemical Reviews, 2001. 101(6): p. 1629-1658), molecular shape rules for surfactant self-assembly (see, e.g., Israelachvili, J. N., et al., Journal of the Chemical Society-Faraday Transactions Ii, 1976. 72: p. 1525-1568; Nagarajan, R., Langmuir, 2002. 18(1): p. 31-38; Schenning, A. P. H. J., et al., Journal of the American Chemical Society, 1998. 120(32): p. 8199-8208), morphologies of phase-separated block copolymers (see, e.g., Jain, S, and F. S. Bates, Science, 2003. 300(5618): p. 460-464; Li, Z. B., et al., Science, 2004. 306(5693): p. 98-101; Cui, H. G., et al., Science, 2007. 317(5838): p. 647-650; Jenekhe, S. A. and X. L. Chen, Science, 1999. 283 (5400): p. 372-375; Ruokolainen, J., et al., Science, 1998. 280(5363): p. 557-560), self-assembly at interfaces (see, e.g., Chandler, D., Nature, 2005. 437(7059): p. 640-647; Bowden, N., et al., Science, 1997. 276(5310): p. 233-235; Zasadzinski, J. A., et al., Science, 1994. 263(5154): p. 1726-1733), and liquid crystals (see, e.g., Ungar, G., et al., Science, 2003. 299(5610): p. 1208-1211; Kato, T., Science, 2002. 295(5564): p. 2414-2418; Gabriel, J. C. P., et al., Nature, 2001. 413(6855): p. 504-508). In this field it is important to understand not only how molecules aggregate on the nanoscale, but also how these nanostructures influence macroscopic material properties. In soft matter, the forces that drive molecules to aggregate are weak and the energy landscapes that describe their conformations and assembly modes are complex. The polymorphism commonly observed in organic crystals suggests that directing self-assembling systems along specific energy pathways is a promising strategy to search for materials with new structures and functions.

Current peptide amphiphile materials can be molecularly designed to present a large variety of bioactive epitopes. However, control over nanofiber length and alignment is difficult to achieve. The present invention provides peptide amphiphile nanofibers significantly longer than previously available (higher aspect ratio) while controlling their directionality and alignment. One major benefit of such materials, for example, is their improved mechanical properties, such as an increase in Young's Modulus, as supported by rheological investigations. One other major benefit is control over the individual nanofiber orientation. This kind of alignment has important implications in environments where an oriented matrix is highly desired. One embodiment of the present invention provides guidance and controlled growth directionality to neuronal cells. This technique also finds use in producing an oriented matrix that comprises bioactive epitopes presented in specific configurations, which are advantageous over a randomly oriented matrix.

The present invention provides compositions comprising assemblies of nanofiber bundles having macroscopic alignment, and methods for generating such nanofiber bundles. Experiments conducted during the course of developing embodiments for the present invention investigated the structural evolution of water-soluble, self-assembling molecules from small aggregates into assemblies of nanofiber bundles that display macroscopic alignment. The nanofiber bundles are not limited to particular size dimensions. In some embodiments, the nanofiber bundles have uniform diameter and contain approximately 20 nanofibers (e.g., 15 nanofibers, 16 nanofibers, 17 nanofibers, 18 nanofibers, 19 nanofibers, 20 nanofibers, 21 nanofibers, 22 nanofibers, 23 nanofibers, 24 nanofibers, 25 nanofibers, 30 nanofibers, 35 nanofibers). The assemblies of nanofiber bundles are not limited to a particular range of ordering. In some embodiments, the range of ordering is extended into at least the centimeter scale by introducing a weak shear force, resulting in a three-dimensional "noodle-like" structure (FIG. 1, A to C) with internal alignment that can be fixed mechanically as gel by divalent ions.

The present application provides a class of peptide amphiphiles (PAs) that comprise a hydrophobic tail, a peptide block that includes β-sheet forming or cross-linking residues, and a charged block (e.g., comprising charged amino acid residues) for, for example, solubility and biological recognition. Upon application of a trigger, for example a change in pH or ion concentration, these PA molecules self-assemble in aqueous solution into fibers. Generally, the amino acids positioned near the tail are bulky β-sheet inducers such as valine, alanine, and leucine. The alkyl chains are in the core of the fibers, with peptide epitopes displayed on the periphery for cell interaction, as shown in FIG. 1. The peptide epitopes that have been incorporated into the PA molecules mimic extracellular matrix proteins with functions, for example, to promote cell adhesion or differentiation through cell signaling. During the course of development of the present invention, a large number of peptide and bioactive epitope variations have been designed and developed, all of which self-assemble into nanofibers.

In some embodiments, the nanofiber bundles are developed from aggregates of peptide amphiphiles (PA). The nanofiber bundles are not limited to particular types of PAs. In some embodiments, the PAs self-assemble into high-aspect-ratio nanofibers (see, e.g., Hartgerink, J. D., et al., Science, 2001. 294(5547): p. 1684-1688, herein incorporated by reference in its entirety). In some embodiments, the PAs are composed of a $V_3A_3E_3$ peptide (i.e., Valine-Valine-Valine-Alanine-Alanine-Alanine-Glutamic Acid-Glutamic Acid-Glutamic Acid) sequence and a $C_{16}$ alkyl tail at the peptide's N-terminus, as shown in FIG. 1D.

The assemblies of nanofiber bundles are not limited to a particular method of production. In some embodiments, production of the assemblies of nanofiber bundles involve, for example, exposing PA aggregates to different temperatures. For example, experiments conducted during the course of development of embodiments for the present invention demonstrated that PA aggregates are metastable at room temperature and spontaneously transform into nanofibers arranged isotropically. However, the state of macroscopic alignment at room temperature is only achieved when PA molecules are reorganized through elevated temperature and subsequently cooled to room temperature. As such, in some embodiments, exposure of room temperature PA aggregates to elevated temperatures organizes the PA molecules into large planar assemblies that, upon cooling, template the formation of macroscopic aligned nanofiber bundles.

Figure 2:
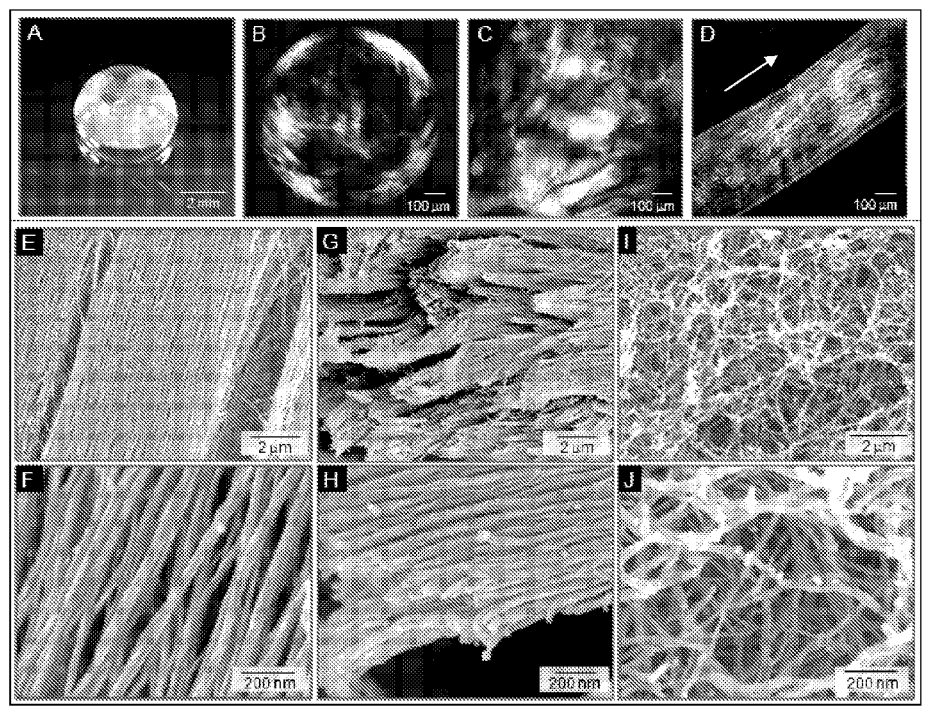
FIG. 2 shows (A) PA solution that was heated to 80° C. and then cooled to 25° C. With the addition of $Ca^{2+}$, heated PA solution forms (B) bubble- and (C) film-shaped gels that appear birefringent between crossed polarizers. (D) Noodle formed by dragging heated PA solution in $Ca^{2+}$ solution shows liquid crystalline alignment along the noodle axis, as indicated by the arrow. (E, F) SEM showing long-range alignment of nanofibers in gels formed from heated PA solution. (G, H) Similar extensive alignment can be seen in PA that was gelled at 80° C. (I, J) Freshly dissolved PA solution after gelling with $Ca^{2+}$ at 25° C. forms a matrix of randomly entangled nanofibers with no preferential orientation. All PA solutions were 1 wt %.

In some embodiments, the assemblies of nanofiber bundles are developed through, for example, dissolving of the PA molecule in pure water at 0.5-1 wt %; heating the dissolved PA molecules at 80° C. for 30 min, and then cooling the PA molecules to 25° C. In such embodiments, the resulting PA solution (FIG. 2A) with added $Ca^{2+}$ formed a four-fold stiffer gel relative to the unheated sample. Using polarized optical microscopy, it was found that gels formed from these heated solutions contained large liquid crystalline (birefringent) domains (FIG. 2B, C). Dragging this PA solution in phosphate buffered saline (PBS) or $Ca^{2+}$ solution were shown to result in a noodle with macroscopic alignment of the liquid crystalline phase along the noodle axis (FIG. 2D). In comparison, the unheated solution did not form such stable structures and was not birefringent. Scanning electron microscopy (SEM) demonstrated that the gel formed from heated PA contained an extraordinarily long array of aligned nanofibers (FIG. 2E, F). Similarly, extensive alignment was observed when a PA solution was gelled with $Ca^{2+}$ at 80° C. (FIG. 2G, H). Unheated PA, however, formed a matrix of randomly entangled nanofibers (FIG. 2I, J). Accordingly, in some embodiments, exposure of room temperature PA aggregates to temperatures near 80° C. (e.g., 50° C., 52° C., 54° C., 56° C., 58° C., 60° C., 62° C., 64° C., 66° C., 67° C., 68° C., 70° C., 72° C., 75° C., 78° C., 80° C., 82° C., 84° C., 86° C., 90° C., 100° C.) for approximately 30 min (e.g., 20 min, 25 min, 30 min, 32 min, 35 min, 40 min) organizes the PA molecules into large planar assemblies that, upon cooling (e.g., to a temperature less than approximately 80° C.; to room temperature), template the formation of macroscopic aligned nanofiber bundles. Lower temperatures may also be used.

Figure 3:
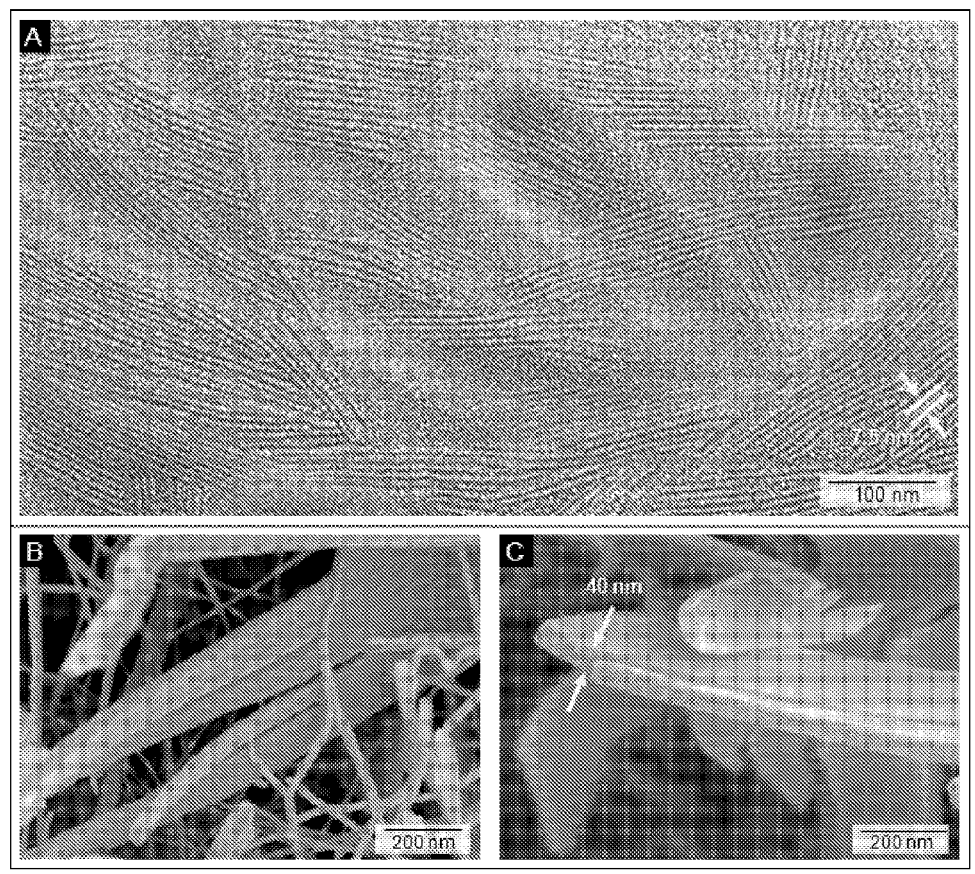
FIG. 3 shows (A) Quick-freeze/deep-etch TEM micrograph of PA solution at 80° C. (B, C) SEM of plaque structures in PA gels formed with $Ca^{2+}$ at 80° C. Some plaques crack into nanofibers bundles and the average thickness of these structures is around 40 nm, as indicated by the arrows.

Experiments conducted during the course of development of the present invention examined the effects of heating on PA microstructure by quick-freeze/deep-etch (QFDE) transmission electron microscopy (TEM). QFDE is a sample preparation technique that allows high resolution imaging of hydrated structures by electron microscopy while minimizing disruption of the sample by fixation or processing. All solutions for QFDE were initially prepared by freshly dissolving the lyophilized PA powder in water (0.5 wt %) at 25° C. The solutions were then studied before heating (25° C.), during heating (80° C.), and after heating and cooling (25° C.). It was shown that the PA microstructure changed considerably during the heating and cooling process. Freshly dissolved PA solution contained a variety of small aggregates, such as micelles, tubes, and vesicles. These aggregates were generally less than 100 nm in diameter and less than a micron in length. After being heated at 80° C. for 30 min, most of the small aggregates disappeared and the solution was primarily composed of larger, sheet-like aggregates that were over a micron in length and width. Some of the sheet-like structures had a periodic surface texture with a spacing of about 7.5 nm (FIG. 3A). The PA solution that had been heated to 80° C. and then cooled to room temperature was composed of locally aligned nanofiber bundles. The fiber bundles were tens of nanometers in diameter and several microns in length. In addition, counterparts of sheet-like structures in SEM samples of PA gelled at 80° C. (FIG. 3 B, C) were identified. In such samples, SEM showed 5-10% of plaque-like structure in addition to the well-aligned fibers bundles seen in FIG. 1G, H. These plaques were about 40 nm in thickness, up to microns in length/width (FIG. 3C) and sometimes appeared to be multilayered. They often contained long parallel striations and, in some cases, appeared to crack into fiber bundles along these striations (FIG. 3 B, C). Using Energy Dispersive X-Ray (EDX), the composition of plaque was determined to be the same as that of the fiber bundles. Similar plaque structures were not observed in the unheated PA solutions or gels. As such, in some embodiments, the present invention provides aligned nanofiber bundles having sheet-like aggregates. In some embodiments, the aligned nanofiber bundles are not limited to particular diameter distances (e.g., tens of nanometers in diameter). In some embodiments, the aligned nanofiber bundles are not limited to particular length distances (e.g., several microns in length).

Experiments conducted during the course of development of the present invention determined that freshly dissolved PA solution contains a variety of metastable, kinetically trapped aggregates. Heating to approximately 80° C. provided this system with enough energy to reorganize the polymorphic aggregates into sheets that, upon cooling, templated the formation of closely associated PA fiber bundles. The local packing geometry, which influences the type of aggregates formed, was shown to be a balance between the effective size of the head group (the peptide segment) and the effective size of hydrophobic alkyl tail (see, e.g., Israelachvili, J. N., et al., Journal of the Chemical Society-Faraday Transactions Ii, 1976. 72: p. 1525-1568). Many factors, including steric interactions, hydration forces, and electrostatic repulsion were shown to affect the head group size. The size of the hydrophobic alkyl tail is primarily influenced by hydrocarbon chain structure and mobility. In some embodiments, the β-sheet, which was observed by circular dichroism (CD) throughout heating and cooling, fixes the distance between PA head groups. In some embodiments, the net charge of the head group is similar at all explored temperatures consider that, for example, counterion condensation does not change significantly with temperature. In some embodiments, as a result of, for example, the strong β-sheet and the relatively unchanged head group charge, the effective PA head group size does not change significantly as the PA is cooled from 80° C. to 25° C. In some embodiments, the volume of the hydrophobic alkyl tail changes with temperature. For example, since the melting point of palmitic acid is 63° C., the alkyl tail should be less ordered at 80° C., and at 25° C. the hydrophobic core is ordered considering the strong β-sheets, as shown for the $V_3A_3$ sequence in this PA, have been shown to correspond to more ordered hydrophobic cores (see, e.g., Jiang, H. Z., Soft Matter, 2007. 3(4): p. 454-462). In some embodiments, the effective volume of the hydrophobic tail decreases with decreasing temperature. In some embodiments, the resulting shape change during cooling is responsible for the observed transition from sheets to fibers.

In some embodiments, the aligned nanofiber bundles are developed from molecules (e.g., PA) having a balance of β-sheet character, head group charge, and alkyl tail hydrophobicity. Experiments conducted during the course of development of the present invention determined that the formation of aligned nanofiber bundles PA molecules requires a balance between the β-sheet forming segment, the charged head group, and the hydrophobic alkyl tail. It was shown that changing any of these components can adjust the balance among them and therefore result in a different self-assembled structure. For example, when the PA has a weaker β-sheet forming segment (such as $A_4G_3$) (see, e.g., Kim, C. A. and J. M. Berg, Nature, 1993. 362(6417): p. 267-270) or a bulkier head group, it is more difficult to use the same process to achieve macroscopic alignment. Similarly, it was shown that when the pH value is adjusted so the PA molecules are more charged, it is harder to form a noodle of aligned nanofibers because of the increased electrostatic repulsion between head groups. In some embodiments, the length and hydrophobicity of the PA alkyl tail is contemplated to influence its ability to form the observed structures.

Figure 4:
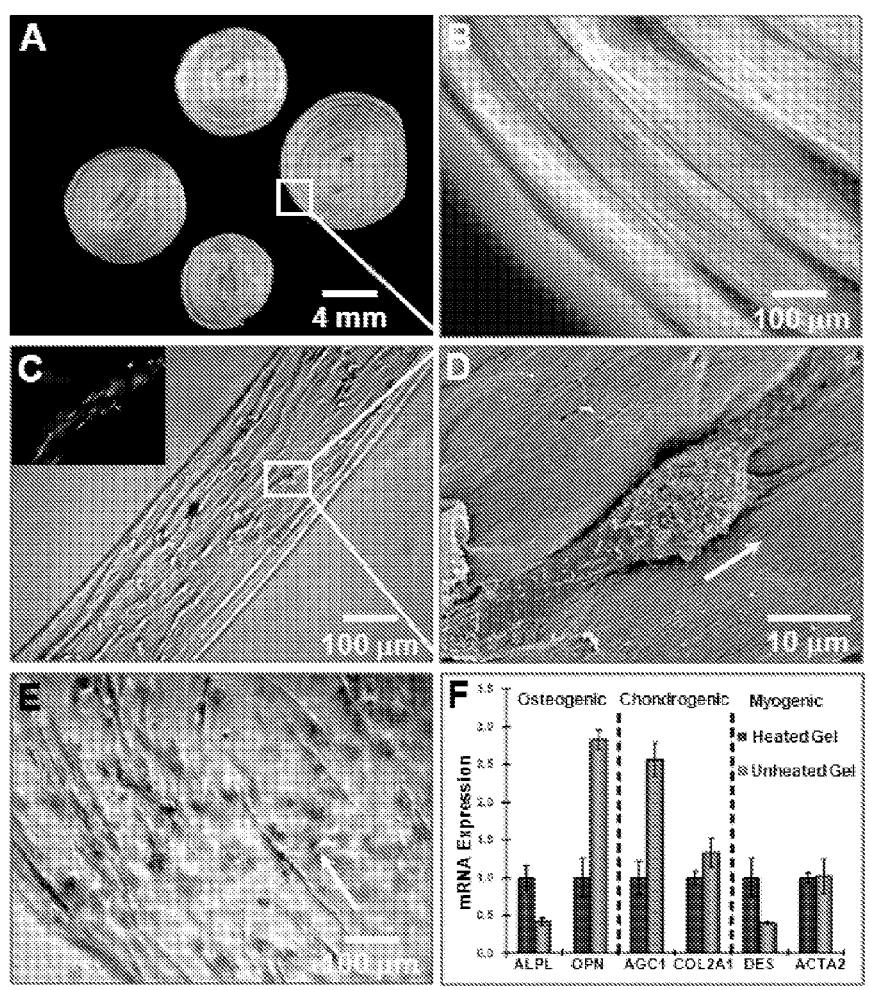
FIG. 4 shows (A) Noodle rolled into a spiral with (B) uniform preferential orientation under crossed polarizers. (C) hMSC encapsulated in the noodle preferentially align with the "noodle" axis. The inset shows calcein-labeled live cells cultured in noodle. (D) SEM image of cells aligning to the oriented PA matrix, arrow indicates the fiber alignment direction. (E) Bubble gel formed with heated PA solution shows some local alignment of cells, as indicated by arrows. (F) hMSC differentiate differently in PA gel with and without heat treatment. Lineage-specific marker genes and housekeeping gene picked were Osteogenic lineage: Alkaline Phosphatase, liver/bone/kidney (ALPL), Osteopontin (OPN); Chondrogenic lineage: Aggrecan (AGC1), Collagen II Alpha I (COL2A1); Myogenic lineage: Desmin (DES), Alpha Smooth Muscle Actin (ACTA2); Housekeeping gene: Glyceraldehyde 3-phosphate dehydrogenase (GAPDH).

The aligned nanofiber bundles are not limited to particular uses. In some embodiments, the aligned nanofiber bundles are used to direct cellular orientation and outgrowth. For example, in FIG. 4A a continuous PA "noodle" was dragged and rolled into a spiral shape on a rotating disk. Polarized optical microscopy showed that long range alignment of PA fiber bundles followed the direction of the dragging force (FIG. 4B). When human mesenchymal stem cells (hMSCs) were seeded in such PA noodles, they started to elongate along the fiber direction within 72 hours (FIG. 4C). Characterization by optical microscopy, fluorescence labeling, and SEM (FIG. 4 C, D) demonstrated that cell bodies and philopodia were aligned with nearby nanofibers. The heating and cooling process also had effects on stem cell differentiation. For example, in FIG. 4E, the hMSCs were mixed with heated and unheated PA solutions, gelled with calcium and cultured for 2 weeks in osteogenic, chondrogenic, or regular growth medium (Cambrex, Walkersville, Md.). Real time RT-PCR revealed that hMSCs cultured in unheated gels were more differentiated compared to heated gels in both osteogenic and chondrogenic differentiation media (FIG. 4F). In growth medium, however, hMSCs were more differentiated towards a myogenic lineage when cultured in heated gels compared to unheated gels. The effects on hMSC orientation result from, for example, contact guidance along the preferentially oriented matrix (see, e.g., Tranquillo, R. T., Cell Behaviour: Control and Mechanism of Motility, 1999(65): p. 27-42). Cells encapsulated in a three-dimensional gel must overcome the physical barriers around them. By proteolysis or by morphological adaptation, the direction of nanofibers alignment is less restricted, therefore favored for cellular orientation and outgrowth. Effects on differentiation, however, result from, for example, the interplay of different mechanical properties and alignment of nanofibers orientation factors (see, e.g., Engler, A. J., et al., Cell, 2006. 126(4): p. 677-89). Accordingly, the aligned nanofiber bundles may be used as cell growth scaffolds the field of regenerative medicine, particularly when orientation and scaffold stiffness can significantly affect the quality of tissue regeneration (e.g., spinal cord and blood vessel engineering) (see, e.g., Xu, C. Y., et al., Biomaterials, 2004. 25(5): p. 877-86; Yang, F., et al., Biomaterials, 2005. 26(15): p. 2603-2610). In some embodiments, the aligned nanofiber bundles are used to guide the spatial arrangement of cells, to control cell outgrowth, and/or to influence the differentiation of stem cells.

In some embodiments, the present invention provides novel hydrogel materials and processing methods to create highly oriented synthetic extracellular matrix, which can be used, for example, to control cellular orientation and outgrowth in both 2-D and 3-D environments. With these materials and methods, arbitrary macro scale (>1 cm) oriented hydrogel matrixes have been rapidly prepared. Birefringence and scanning electron microscopy (SEM) observations revealed that these macroscopically oriented matrixes are composed of highly aligned nanofiber arrays. In some embodiments, the aligned fiber matrix provides physical guidance over cellular orientation and outgrowth. The present invention is not limited to particular hydrogel materials. In some embodiments, the hydrogel materials were self-assembled from surfactant peptide molecules (see, e.g., Hartgerink, J. D., E. Beniash, and S. I. Stupp, Science, 2001. 294(5547): p. 1684-1688). In some embodiments, the hydrogel materials are bioactive (see, e.g., Niece, K. L., et al., Journal of the American Chemical Society, 2003. 125(24): p. 7146-7147; Beniash, E., et al., Acta Biomaterialia, 2005. 1(4): p. 387-397). In some embodiments, so as to accommodate specific needs of different cell types, the matrix was customized chemically by inserting signaling peptide sequences into these nanofibers and mechanically by changing the hydrogel concentration.

In some embodiments, the aligned nanofiber bundles are used to create desired surface coating patterns that guide cellular orientation and outgrowth, and/or a route for fabricating a patterned in vitro neuron network. In some embodiments, the aligned nanofiber bundles are used to form, for example, a "biological wire" that can transmit signals between biological and/or artificial devices. In some embodiments, the aligned nanofiber bundles are used to fabricate multi-layer ECM analogs with different cellular orientations and compositions. In some embodiments, the aligned nanofiber bundles are used to template oriented biomineralization.

Figure 19:
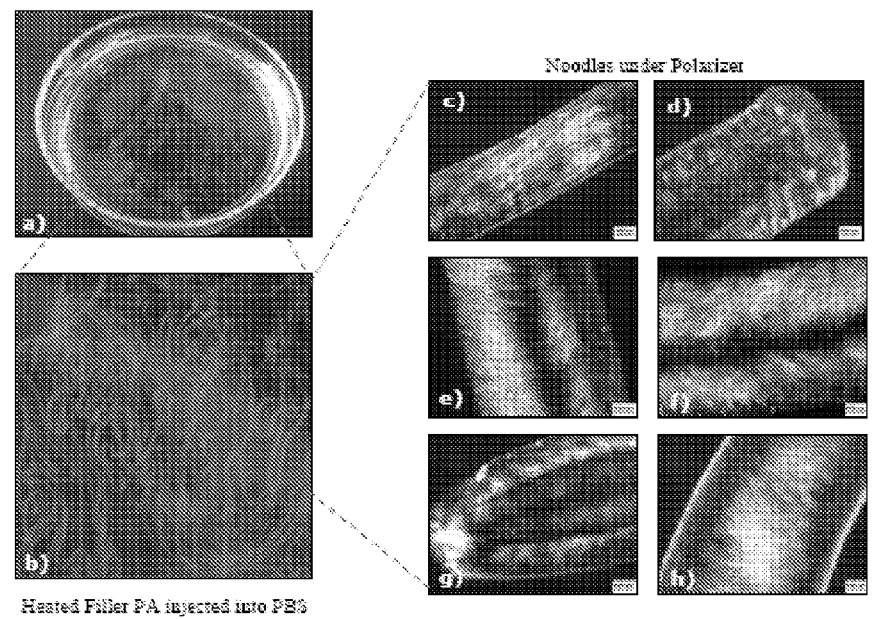
FIG. 19 shows processing of heat treated PA materials into elongated "noodle-like" structure. (a-b) this structure is formed by injecting heat treated PA solution in PBS or Ca2+ solution. (c-h) Zoom in view. Birefringence in these zoom in images clearly indicates that these structures comprise aligned nanofibers. Injection parameters such as injection velocity and directionality, flow rate, and syringe geometrical configurations have significant effect on the resulting "noodle-like" structure.

Implantable applications using the compositions comprising aligned nanofiber bundles and methods of the present invention are also contemplated. For example, compositions of the present invention are used to create self-assembled matrices (such as those made with PA materials) that stimulate cells and tissues in vivo through both a biochemical stimuli and a physical stimuli provided by the aligned nanofibers. Implants of appropriate materials with advantages of controlling nanofiber length and alignment include, for example, skin (e.g., in patients with burns), smooth muscle (e.g., to align and provide a biomimetic environment for vascular tissue), ligaments and tendons (e.g., to augment fibroblast growth in ligament or tendon repair during traumatic tiers), etc. Another example includes benefits for neuronal tissue. For example, PA materials comprising the peptide sequence IKVAV (SEQ ID NO.:12)(e.g., for recruitment and differentiation of neuronal stem cells) have been applied to promote healing of neuronal tissue after spinal cord injury. By delivering this PA material through a system similar to that described in FIG. 19, the aligned nanofibers enhance neuronal bridging and repair by providing nanotextures for cell migration.

The present invention provides a process to produce matrices with aligned nanofibers. It is contemplated that applications using the present invention expands beyond biological or biomedical application. For example, the present invention provides a method to organize self-assembled materials at the nanoscale. Therefore, materials could be molecularly designed with enhanced electrical properties for electronic applications. In these kinds of materials, for example, enhancement of electrical properties (e.g., current conduction) results from controlling the alignment of the individual nanofibers. An additional application is to combine the process as described herein with rapid prototyping techniques. Doing so would permit the creation of highly ordered patterns for a variety of applications in biology, biosensors, electronics, and the like.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); and ° C. (degrees Centigrade).

Example 1

Figure 5:
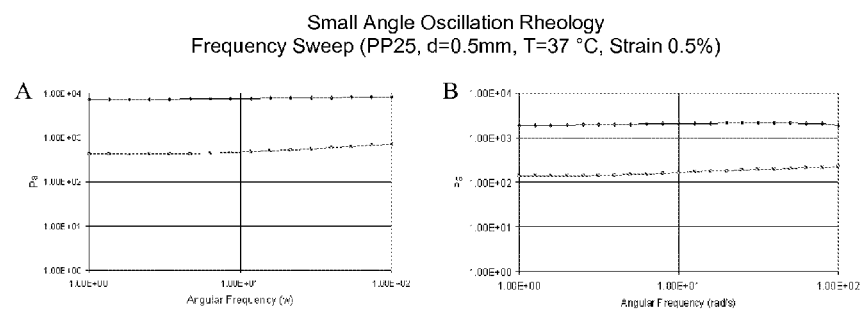
FIG. 5 shows a frequency sweep of a gel formed with PA (A) after heat treatment and (B) before heat treatment.

This example describes the materials and methods for rheology experiments and Quick-freeze deep-etch (QFDE) sample preparation for analysis and characterization of materials. Rheological data were collected with a Paar Physica Modular Compact Rheometer 300 operating in 25 mm parallel-plate configuration. All samples had a total volume of 300 µL. Once the gels were formed, the top plate was lowered onto samples to a gap distance of 0.5 mm. Mineral oil was dropped around the edge of the plate and wet tissues were placed at the perimeter of a chamber around the gel to minimize evaporation. Stage temperature was maintained at 37° C. by a Peltier heating system. Samples were allowed to equilibrate one hour before testing. Strain sweeps were preformed on all samples to determine the linear viscoelastic regime. Gels were tested at 0.5% oscillatory strain from 100 to 1 rad/s. G' and G" were averaged over a minimum of two trials. Samples were prepared by gelling 0.75 wt % PA ($C16V_3A_3E_3$) solutions (with or without heat treatment) with $Ca^{2+}$ (see, FIG. 5).

Figure 6:
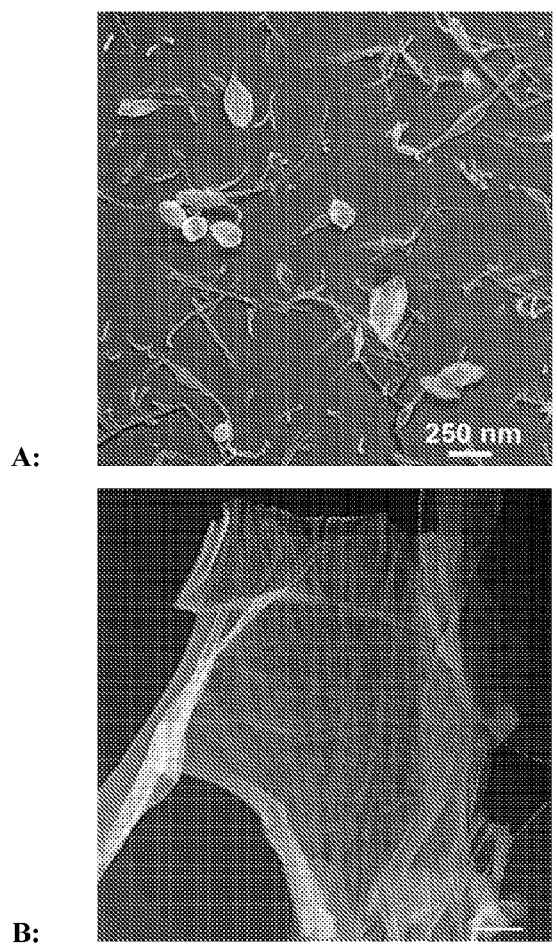
FIG. 6 shows Quick-freeze/deep-etch TEM micrographs of (A) freshly dissolved PA solution at 25° C. (B) PA solution after heating to 80° C. and cooling to 25° C.

Regarding QFDE sample preparation, a 30-uL aliquot of sample was placed on an aluminum tab and slam frozen (Gentleman Jim Slam Freezing Apparatus) onto a copper block chilled to liquid nitrogen temperature (−195° C.). After transfer into a freeze-fracture apparatus (Model CFE-40; Cressington Scientific Instruments, Watford, UK), the frozen sample was fractured, etched for 25 minutes at −95° C., and rotary shadowed with a platinum-carbon mixture at a 20° angle and then strengthened with carbon evaporated from a 90° angle overhead. The resulting replica is then separated from the organic sample and mounted on a copper grid for TEM observation (see, FIG. 6).

Example 2

This example describes the synthesis of peptide amphiphiles. The peptide amphiphiles with a C-terminal carboxylic acid were synthesized on a 0.25-1 mmol scale (see, e.g., Hartgerink, J. D., et al., PNAS USA, 2002. 99(8): p. 5133-8). Briefly, the peptide sequence, such as VVVAAAEEE, (SEQ ID NO.:7), was synthesized using an automated peptide synthesizer and Fmoc chemistry starting from pre-functionalized Wang resin. Following Fmoc removal from the final residue, hexadecanoic acid (Aldrich) was conjugated to the free N-terminus. The alkylation reaction was accomplished by using eight equivalents of the fatty acid, eight equivalents O-Benzotriazole-N,N,N',N'-tetramethyl-uronium-hexafluoro-phosphate (HBTU) and 12 equivalents of diisopropylethylamine in 1:1 dimethylformamide and dichloromethane. The reaction was allowed to proceed for at least 6 hours until the ninhydrin test (Kaiser Assay) was negative. Cleavage of peptide amphiphile from the resin and side-chain protection was carried out in 95% trifluoroacetic acid, 2.5% $H_2O$, 2.5% triisopropylsilane at room temperature for 2 hours. The cleavage mixture and two subsequent dichloromethane washings were filtered into a round-bottom flask. This solution was concentrated by rotary evaporation to a thick viscous solution. The crude PA was isolated by precipitating with cold diethyl ether, filtrating, washing with copious cold ether, and drying under vacuum.

To purify the synthesized peptide amphiphile the resulting material was dissolved in water at a concentration of 10 mg/ml with the addition of $NH_4OH$ to adjust the pH of the solution to 9. The solution was then filtered through a 0.2-µm nylon Acros filter and purified by preparative-scale high-performance liquid chromatography (HPLC). Collected fractions were analyzed by electrospray ionization mass spectrometry (ESI-MS) and confirmed targets were combined and lyophilized. After lyophilization, the white powder was combined and re-dissolved in PBS at a concentration of 10 mg/ml. The pH of this solution was gradually adjusted to 7.00 by adding 0.5M NaOH and monitoring with pH meter. Excess salt was then removed by dialyzing this solution against pure water. This step ensured that peptide amphiphile molecules were uniformly ionized and therefore minimized batch to batch variation. After dialysis, the solution was re-lyophilized and stored in −20° C. freezer before use.

Example 3

Figure 7:
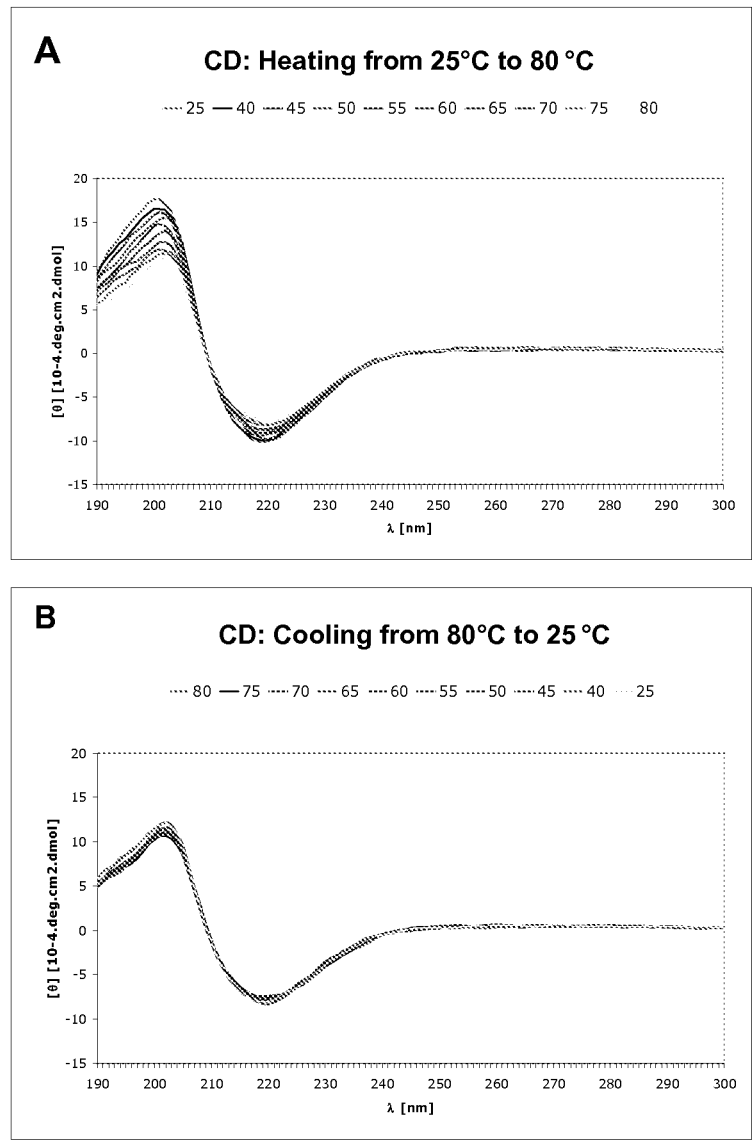
FIG. 7 shows CD scans from 0.01 wt % PA ($V_3A_3E_3$) solution at different temperatures during heating up and cooling down cycle. (A) Scan while heating up. (B) Scan while cooling down.

This example describes Circular Dichroism (CD) data. Circular dichroism was used to study how elevated temperature affects the secondary structure of peptide amphiphiles. The CD signal was recorded (J-715 CD spectrometer, JASCO Inc., Easton, Md.) during heating from 25° C. to 80° C. and then during cooling from 80° C. to 25° C. (see FIG. 7). A strong beta sheet signature was seen over all the temperature range covered. The CD signal of freshly dissolved filler PA solution slightly decreased as temperature increased from room temperature to 80° C. but changed little during cooling from 80° C. to 25° C. (see, e.g., Meijer, J. T., et al., Langmuir, 2007. 23(4): p. 2058-2063).

Example 4

Figure 8:
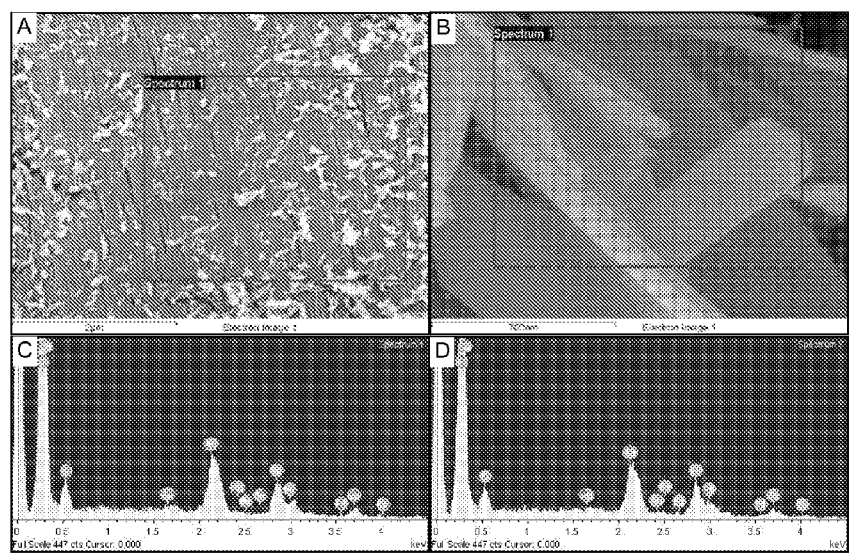
FIG. 8 shows EDX data. EDX data shows composition of fiber bundles and plaque structures formed by $Ca^{2+}$ induced gelation at 80° C. are very similar. (A, B) SEM micrographs of fibers and plaque regions. (C, D) EDX composition spectrum collected from boxed regions in A and B, quantitative data is listed in Table 1.

This example describes EDX data. EDX data shows that the elemental composition for the plaque structures and fibers are the same. EDX data shows composition of fiber bundles and plaque structures formed by $Ca^{2+}$ induced gelation at 80° C. are very similar. (FIG. 8A, B) SEM micrographs of fibers and plaque regions. (FIG. 8C, D) EDX composition spectrum collected from boxed regions in A and B, quantitative data is listed in Table 1.

TABLE 1

EDX composition analysis of fibers and plaque structure formed by $Ca^{2+}$ induced gelation at 80° C.

| | Fibers Composition | | | Plaque Composition | |
|---|---|---|---|---|---|
| Element | Weight % | Atomic % | Element | Weight % | Atomic % |
| C K | 42.56 | 79.84 | C K | 41.28 | 80.33 |
| O K | 7.99 | 11.25 | O K | 6.96 | 10.17 |
| Ca K | 2.87 | 1.61 | Ca K | 2.69 | 1.57 |
| Pd L | 20.28 | 4.29 | Pd L | 20.95 | 4.60 |
| Au M | 26.31 | 3.01 | Au M | 28.11 | 3.34 |
| Totals | 100.00 | | Totals | 100.00 | |

Example 5

This example describes the culturing of hMSCs. hMSCs were cultured in heated or unheated bubble gels (FIG. 4E) for two weeks in hMSC osteogenic, chondrogenic, or regular growth medium (Cambrex, Walkersville, Md.). After culturing, RNA was isolated and reverse transcribed into cDNA with TRIZOL® Reagent and SuperScript® III First-Strand Synthesis System from Invitrogen. Real time PCR was done with Bio-Rad iQ5 Real-Time PCR system and Promega's Plexor® qPCR System.

Several lineage specific marker genes and housekeeping genes were picked for real time RT-PCR (Alkaline Phosphatase, liver/bone/kidney (ALPL), Osteopontin (OPN), Aggrecan (AGC1), Collagen II Alpha I (COL2A1), Desmin (DES), Alpha Smooth Muscle Actin (ACTA2) and Glyceraldehyde 3-phosphate dehydrogenase (GAPDH)). Primer pair sequences are listed in Table 2.

The result shows that, in osteogenic medium, hMSCs cultured in unheated bubble gels express less early marker of ALPL but more later stage marker of OPN (see, e.g., Aubin, J. E., et al., Bone, 1995. 17(2): p. S77-S83). In Chondrogenic medium, hMSC cultured in unheated bubble gels express more of both AGC1 and COL2A1. hMSC cultured in unheated bubble gels were more differentiated compared to heated bubble gels in both osteogenic and chondrogenic differentiation medias (FIG. 4F). In growth medium, however, hMSCs have more DES, indicating they were more differentiated towards a myogenic lineage when cultured in heated gels compared to unheated gels.

TABLE 2

Primer Pair Sequences for Lineage Specific Marker Genes

| Osteogenic Lineage | Alkaline Phosphatase, liver/bone/kidney (ALPL)<br>ACCTCGTTGACACCTGGAAGTC<br>ACGTTGTTCCTGTTCAGC (SEQ ID NO: 01)<br>Osteopontin OPN<br>GTGATGTCCTCGTCTGTAGCAT<br>CAGTAGACACATATGATGGCCG<br>AGG (SEQ ID NO: 02) |
|---|---|

TABLE 2-continued

Primer Pair Sequences for Lineage Specific Marker Genes

| Chondrogenic Lineage | Aggrecan (AGC1)<br>TGTCCACAAAGTCTTCACCTGT<br>GTAGGTGAGGACCGTCTACGTG<br>CAT (SEQ ID NO: 03)<br>Collagen II Alpha I (COL2A1)<br>TGGTGAAAGAGGACGGACTGGA<br>CCAGCAGGACCGACAGGAC (SEQ ID NO: 04) |
|---|---|
| Myogenic Lineage | Desmin DES<br>AGATGGCCCTGGATGTGGAGCC<br>CTTTGCTCAGGGCTGGT (SEQ ID NO: 05)<br>Alpha Smooth Muscle Actin (ACTA2)<br>CTGTGCTTCGTCACCCACGTAG<br>ATGCTCCCAGGGCTGTTTTC (SEQ ID NO: 06) |

Example 6

This example describes the methods for preparation of materials for use generating aligned nanofibers (Example 7), alignment of cells (Example 8), and characterization of properties of the materials (Example 9).

Amino acids and derivatized resins were purchased from Nova Biochem. All chemicals were purchased from Fisher or Sigma-Aldrich and used as provided. All water used was deionized with a Millipore Milli-Q water purifier operating at a resistance of 18.2 MΩ.

Human mesenchymal stem cells (Poietics™ hMSCs), human bladder smooth muscle cells (Clonetics™ bSMCs) and their growth media were all purchased from Lonza (Walkersville, Md.). hMSCs used in the experiments were at passage 6-9 and bSMCs used were at passage 7-10. DRG cells were obtained by digesting freshly acquired DRG tissue from CD-1 mice at postnatal day 1. The DRG were treated with 0.25% trypsin for 30 min at 37° C. and then mechanically dissociated by trituration. The DRG cells were cultured in DMEM/F-12 with 10% FBS, 1% pen/strep, 25 ng/ml nerve growth factor (NGF) and 20 micromolar Cytosine β-D-arabinofuranoside (Ara-C) (Sigma-Aldrich), an anti-proliferative agent to remove all non neuronal cells.

Materials used in this study are peptide amphiphile molecules and their mixtures as shown in FIG. 1. Similar derivatives have also been synthesized and used in other studies (Table 3).

TABLE 3

Peptide Amphiphile Derivatives.

Figure 9:
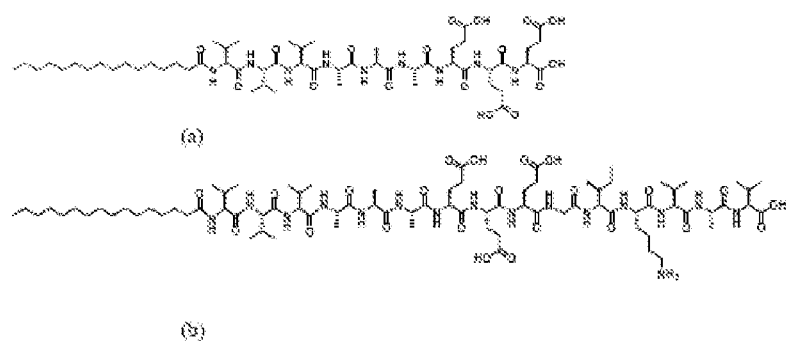
FIG. 9 shows peptide amphiphiles. (A) PA1: $C_{15}H_{31}CO$—VVVAAAEEE(OH) (SEQ ID NO.:7); (B) PA2: $C_{15}H_{31}CO$—VVVAAAEEEGIKVAV(OH) (SEQ ID NO.:8).

| PA1 | $C_{15}H_{31}$CO-VVVAAAEEE(OH) (SEQ ID NO: 07)<br>(See, FIG. 9A) |
|---|---|
| PA2 | $C_{15}H_{31}$CO-VVVAAAEEEGIKVAV(OH) (SEQ ID NO: 08)<br>(See, FIG. 9B) |
| PA3 | $C_{15}H_{31}$CO-VVVAAAEEEGRGDS(OH) (SEQ ID NO: 09) |
| PA4 | $C_{15}H_{31}$CO-VVVAAAEEEGS(P)G(OH) (SEQ ID NO: 10) |
| PA5 | $C_{11}H_{23}$CO-VVVAAAEEESGGGYYPVHPST($NH_2$)<br>(SEQ ID NO: 11) |

Phase Contrast Light Microscopy The interactions between cells and the aligned PA nanofibers were visualized using a phase-contrast light microscope. To help visualizing the alignment of the cells inside PA Noodle, live hMSCs and bSMCs cells were labeled with Calcein Am (Invitrogen, Carlsband, Calif.) after 3 days culture in media. The labeling was done by submerging PA Noodle in 5 mM Calcein Am solution for 30 min at 37° C.

Scanning Electronic Microscopy SEM was employed to study the morphology of cells grown in the PA Noodle. Samples with encapsulated cells were fixed in 1× phosphate buffer containing 2% glutaraldehyde (Electron Microscopy Sciences, Fort Washington, Pa.) and 3% sucrose at 4° C. and pH 7.4. After fixation, the samples were dehydrated using a gradient of 10% to 100% ethanol and critical point dried with Polaron critical point dryer (Model 3100). These samples were sputter-coated with a 4-nm coating of Au/Pd and imaged with a Hitachi S-4800-II SEM.

Example 7

This example describes the generation of and characterization of aligned nanofibers.

Figure 10:
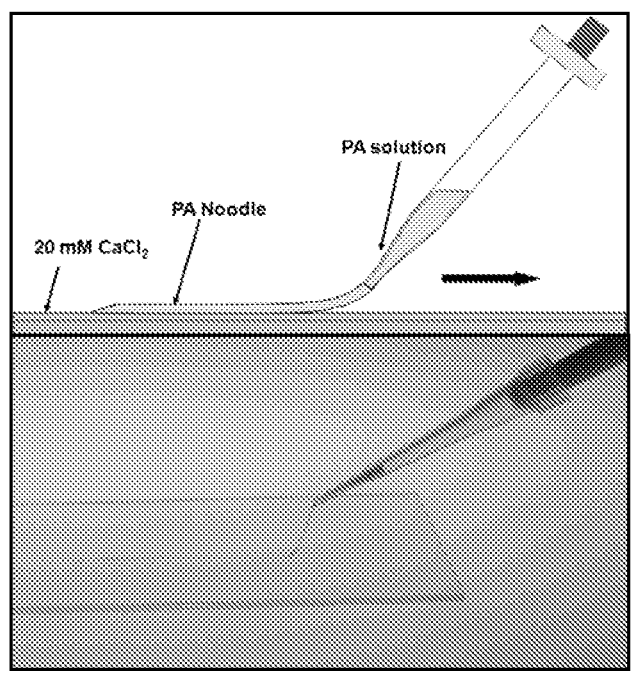
FIG. 10 shows heated and cooled peptide amphiphile solution dragged and gelled into PA Noodle on glass substrate soaked with gelling reagent. Trypan blue was added to peptide amphiphile solution for better visualization.

Fabricating Preferentially Aligned PA Matrix The peptide amphiphiles (PAs) were dissolved in either pure water or phosphate-buffered saline (PBS) at concentrations of 0.5 wt % to 1 wt %. A vortexer was used to help dissolve samples, as needed. The solutions were heated to 80° C., held at that temperature for about 30 min, and then slowly cooled the solution down to room temperature. Dip-coating with the resulting solution, long-range alignment of peptide amphiphile nanofibers on surfaces can be created. Pipetting and dragging this solution in 20 mM $CaCl_2$ solution (FIG. 10) results in a noodle-like gel composed of highly aligned nanofibers. The materials (henceforth called "PA Noodle") were rinsed and collected with water or culture media for further studies.

Figure 11:
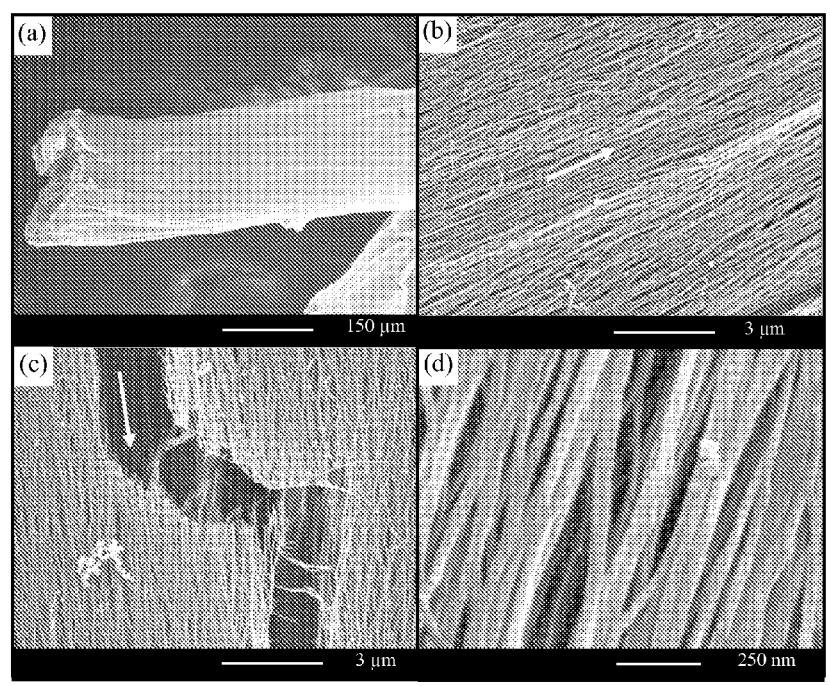
FIG. 11 shows SEM micrographs of aligned PA Noodle. (A) overall image of an oriented PA Noodle, (B) zoom in images of (a) arrow indicates nanofibers orientation, (C) inside the crack (indicated by arrow), nanofibers alignment is just as good as on the surface, (D) nanofibers are perfectly aligned to the nanometer scale.

SEM micrographs of 1 wt % PA Noodle are shown in FIG. 11. SEM observations revealed that the PA Noodle comprises aligned nanofibers and therefore represents a highly aligned nanofibrous scaffold. The three-dimensional structure consists of fiber bundles with diameters around 20-30 nm and majority of the nanofibers are oriented along the longitudinal axis. The PA Noodle was also examined using an optical microscope with and without crossed polarizers (FIG. 12) to investigate birefringence effects. The uniform brightness in FIG. 12(b) indicates, for example, that the high level of nanofiber alignment observed by SEM exists throughout the whole PA Noodle sample.

Example 8

This example describes the results of cellular orientation with aligned nanofibers.

Controlling Cellular Orientation with PA Noodle: 80-90% confluent hMSCs or bSMCs on tissue culture flask were treated with 0.5% Tripsin/EDTA. After the cells detached from the flask, their number was counted with a hemocytometer. For PA coated 2-D surfaces, cells were just randomly seeded on top. To encapsulate them inside PA Noodle, free floating cells were centrifuged into pellet. Heated and cooled PA solution was used to re-suspend the cells pellet at a density of 1000-5000 cells/μl. The PA solution concentration for hMSCs was 0.75-1.0 wt % and 0.5 wt % for bSMCs and DRG cells respectively. After the cells were encapsulated in the PA Noodle, they were cultured in corresponding media and incubated at 37° C. Media were changed every 3 or 4 days.

Figure 12:
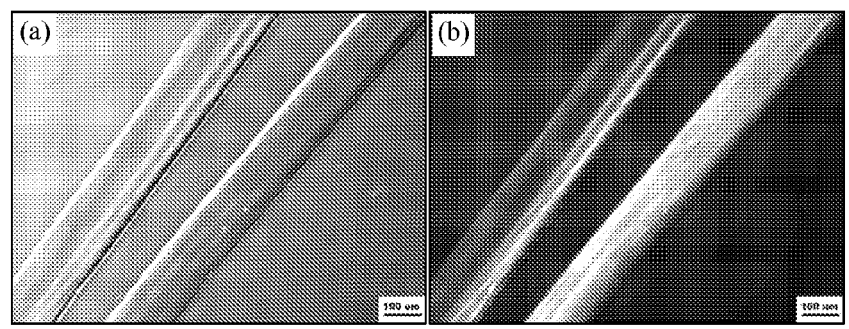
FIG. 12 shows PA Noodle observed under optical microscope without (a) and with (b) crossed polarizers. The uniform birefringence seen in (b) indicates overall alignment of nanofibers inside PA Noodle.

The cellular experiment results indicate that the highly oriented PA Noodle matrix effectively controlled the orientation and outgrowth of three different cell types (hMSCs, bSMCs and DRG cells), presenting a simple method to promote cell alignment on coated 2-D surfaces and in 3-D matrixes. As shown in FIG. 12, bSMCs cultured on top of PA Noodle coated glass maintained bipolar spindle shapes and oriented in the same directions as nanofibers in substrate coating. In contrast, bSMCs grew in random directions on bare glass. Since cell alignment to patterned surface topography is a commonly observed phenomenon (see, e.g., Bellairs R, C. A., Dunn G, Cell behavior. Cambridge: Cambridge University Press, 1982: p. 247-280), it is likely that contact guidance played a role in these results.

Figure 13:
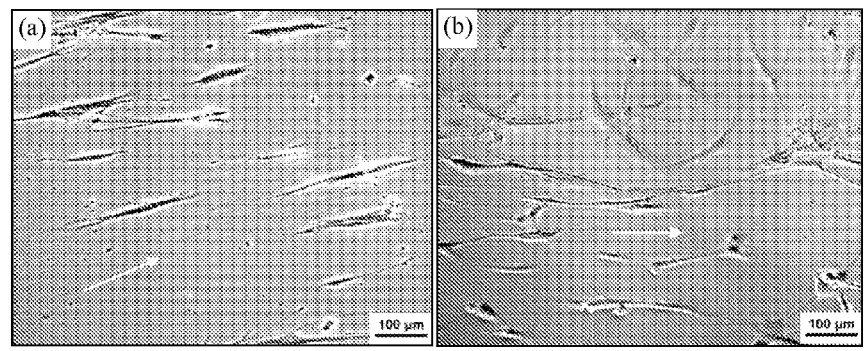
FIG. 13 shows optical micrographs showing bSMCs alignment with PA Noodle coating on glass a) bSMCs grew on coated glass maintained a bipolar shape and oriented in the same direction as substrate nanofibers. b) bSMCs grew in random directions on bare glass (upper half), but in parallel on coating (bottom half). Arrows indicate surface nanofibers orientation.

Interestingly, encapsulated hMSCs extended and preferentially aligned in 0.75 wt % PA Noodle after 3 days of incubation (FIG. 13(a), 13(b)). As cells were distributed in a truly 3-D environment, many fluorescents cells in these figures were out of focus plane. Since seeding density can play a pivotal role in a variety of cell dynamics and hence cell orientation (see, e.g., Bohlin K., O.L.C.I., Methods in Cell Science, 1996. 18(4): p. 329-341(13)), bSMCs were seeded at density of 1000 and 5000 cells/μl in 0.5 wt % PA gel (FIG. 13(c), 13(d)). The cellular alignment pattern of hMSCs compared to bSMCs was similar in different culture conditions. As such, the PA Noodle system is capable of achieving high cellular density with directed alignment of bSMCs in a 3-D environment. In blood vessel engineering, such alignment of SMCs is important since natural vessels are composed of axially aligned SMCs in regions of vortex blood flow (see, e.g., Liu, S. Q., et al., American Journal of Physiology-Heart and Circulatory Physiology, 2003. 285(3): p. H1072-H1080).

Figure 14:
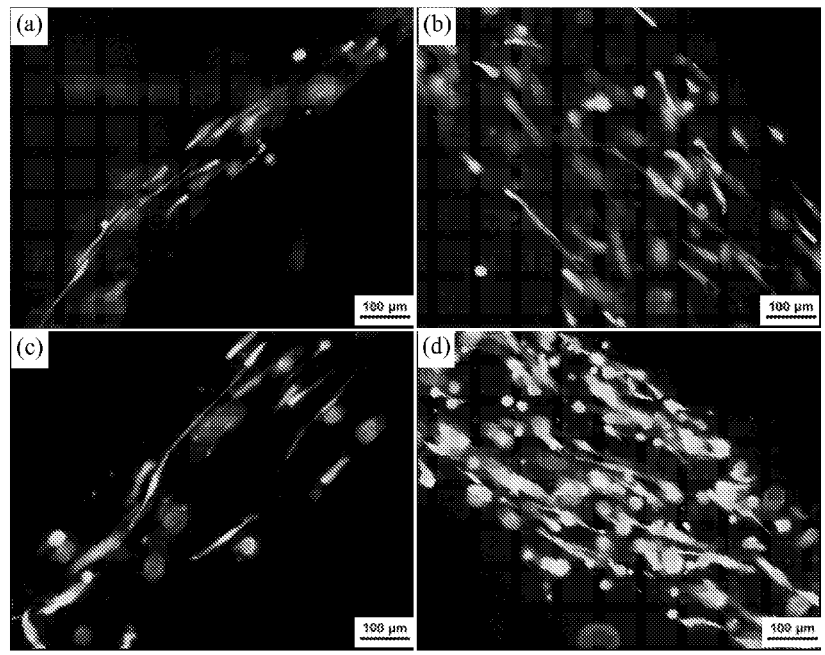
FIG. 14 shows optical micrographs of hMSCs and bSMCs cultured in PA Noodle; (a)-(b) hMSCs seeded in 0.75 wt % PA Noodle at 1000 cells/μl and 2500 cells/μl densities (c)-(d) bSMCs seeded in 0.5 wt % PA Noodle at 1000 cells/μl and 5000 cells/µl densities. Both cell types were labeled with Calcein Am after 3 days culture to help visualization.

Representative SEM micrographs of cells (hMSCs) cultured in a PA Noodle are shown at different magnifications in FIG. 14. The cell body had an apparent bipolar elongated morphology, which follows the same direction of PA nanofibers. Cell filopodia are partly embedded and tightly grabbing to the fibers. Totally encapsulated cells interact with surrounding matrix is difficult to visualize with SEM. However, it is clear that cells are interacting with PA and their orientation has a close relation with the surrounding nanofibers. Unlike 2-D surfaces, encapsulated cells in 3-D matrixes must overcome a greater physical resistance imposed by spatial barriers. By proteolysis or by morphological adaptation, the nanofiber direction is spatially less restricted; therefore cells preferentially orient in this direction.

Figure 15:
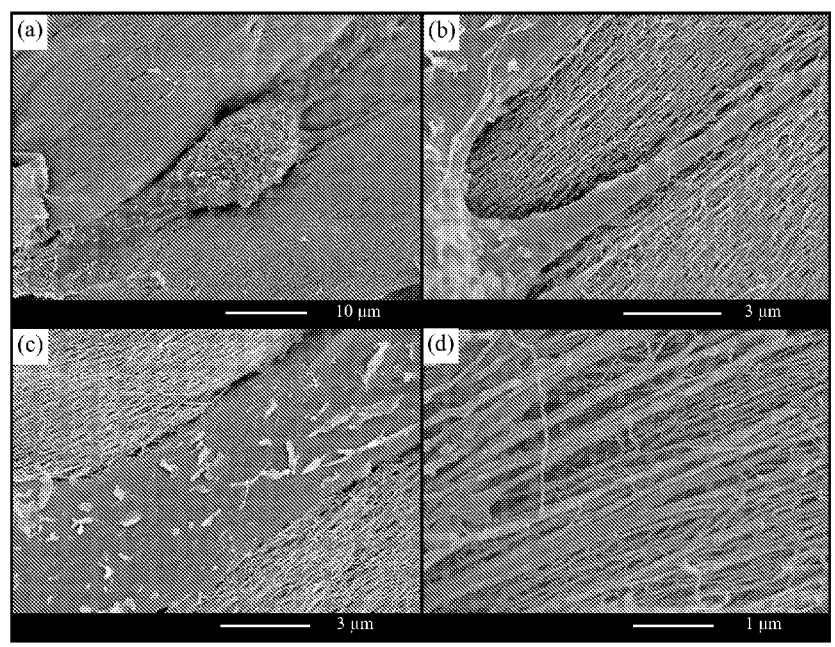
FIG. 15 shows SEM micrographs showing hMSCs aligned with oriented peptide amphiphile matrix; (a) hMSCs interacting with oriented PA matrix; (b-d) zoom in images of (a). Both cell body and filopodia are aligned with nearby nanofibers.
Figure 16:
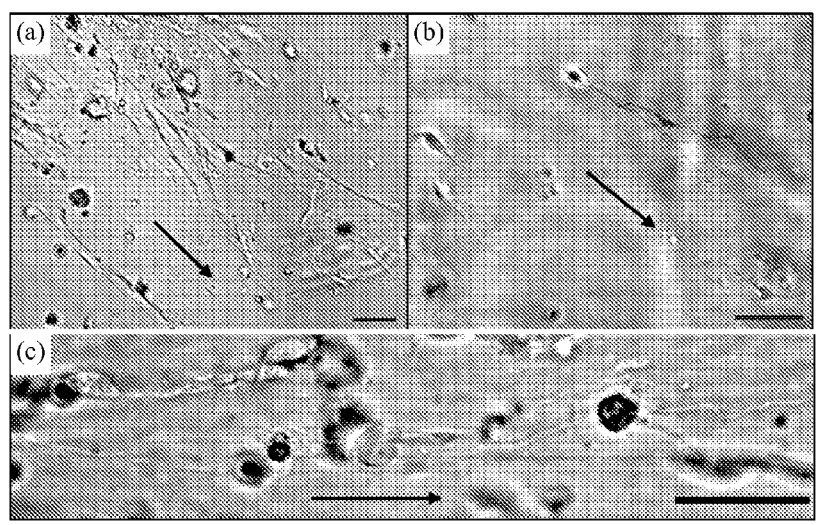
FIG. 16 shows optical micrographs of DRG cells encapsulated in PA Noodle after 3 days, arrows indicate PA Noodle axis, which is also the matrix nanofibers orientation, bar represent 50 um.

Applications in neuron applications was explored. As previously studied by Silva et al. (see, e.g., Silva, G. A., et al., Science, 2004. 303(5662): p. 1352-5), nanofibers with a high density of IKVAK (SEQ ID NO.:13) epitopes caused more selective differentiation of neural progenitor cells to neurons. The gel composition for DRG cells was adjusted by adding 10% of PA2, which contained the IKVAV (SEQ ID No.:12) epitope (FIG. 15). The mixture of PA molecules was then treated in the same way as previously described. Freshly retrieved DRG cells were disassociated and then suspended in the PA Noodle at a density of 5000 cells/μl. Since DRG cells are much smaller than hMSCs and bSMCs, this system was expected to tolerate an even higher cell density. Phase-contrast light microscopy showed that after 3 days, DRG cells have their neurites preferentially aligned along the PA nanofiber direction (FIG. 16). Preferential orientation can be observed on different focus planes. Since freshly retrieved DRG contains of many glial cells, which may proliferate, Ara-C media was added to suppress their growth, and only allow neuron cells to grow in these materials (see, e.g., Billingsley, M. L. and H. G. Mandel, Journal of Pharmacology and Experimental Therapeutics, 1982. 222(3): p. 765-770). Factors, such as $Ca^{2+}$ concentration, gel stiffness and time of tripsin/EDTA treatment, influenced the well being of neuron cells in PA Noodle.

Example 9

Figure 17:
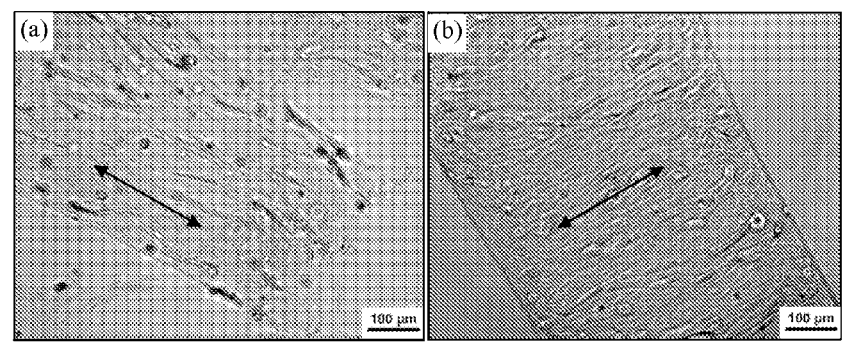
FIG. 17 shows optical micrographs showing preferential cellular orientations are different in PA Noodles formed by dragging or extruding process. (a) In dragging process, elongation flow aligned nanofibers along PA Noodle axis, encapsulated hMSCs therefore aligned parallel to this direction. (b) In extrusion process, shear flow aligned nanofibers perpendicular to PA Noodle axis, encapsulated hMSCs therefore aligned perpendicular to this direction.

This example describes the mechanical and chemical properties of the aligned nanofibers. A distinct character of PA Noodle is the preferential alignment of composing nanofibers, which subsequently leads to preferential cellular orientation and outgrowth. To manipulate this orientation factor in device fabrication, the shear forces applied to nanofibers during gelling process need to be controlled. As shown in FIG. 17, two cells containing PA Noodles were made by dragging (a) and extruding (b) the same PA/Cells mixture in $Ca^{2+}$ gelling reagent. Although compositions were the same, cellular orientations in these two PA Noodles were apparently different (in 9(a), cells grew in parallel to the PA Noodle axis while in 9(b) they grew in perpendicular). This result indicated that the composing nanofibers were orientated differently with elongation flow (dragging) and shear flow (extruding) (see, e.g., Ide, Y. and Z. Ophir, Polymer Engineering and Science, 1983. 23(5): p. 261-265). As such, it was concluded that cellular orientation is a consequence of nanofiber orientation. Accordingly, the present invention provides methods to create ordered cellular structures in a controllable fashion.

Figure 18:
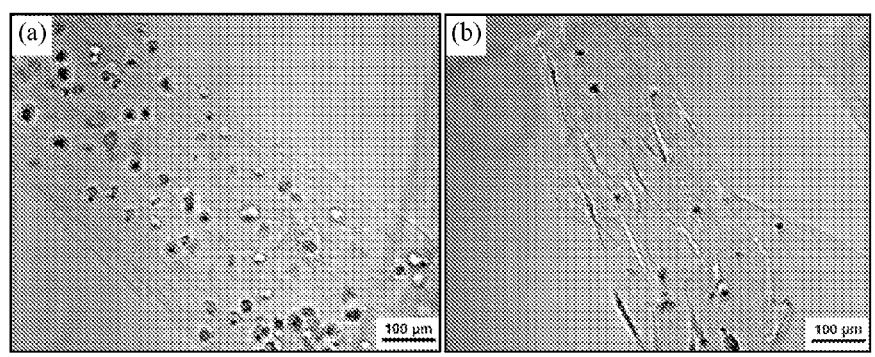
FIG. 18 shows optical micrographs showing PA concentration changes morphologies of encapsulated cells. (a) In 1.5 wt % PA Noodle, encapsulated hMSCs stay rounded morphology after 3 days of culturing. (b) However, in 0.75 wt % PA Noodles, they exhibit bipolar spindle shape after the same culturing time.

In addition to nanofiber orientation, PA Noodle materials are also tunable with respect to mechanical properties. It is already known that optimal matrix stiffness is not the same for all cell types. In the case of hMSC, the matrix stiffness alone can have profound effects in cell fate (see, e.g., Engler, A. J., et al., Cell, 2006. 126(4): p. 677-89). With the PA Noodle system, optimal mechanical properties for each cell type can be adjusted by changing the concentration. For example, hMSCs cultured in PA Noodle of more than 1 wt % concentration were found to maintain a rounded morphology (FIG. 18(a)). However, when the concentration was decreased to 0.75 wt %, hMSCs were mostly bipolar spindle shape (FIG. 18(b)), indicating a contractile phenotype. The results also showed bSMC and DRG cells spread out faster in gel of 0.5 wt % or less.

The chemical composition of the PA Noodle can also be adjusted by adding signaling or cytokine-binding molecules. As an example, in the DRG cells experiment, PA 1 was mixed with the complementary PA 2 bearing the epitope IKVAV, which is believed to be beneficial for neuron cells. Addition of such signaling molecules did not bring any significant change to fiber alignment or overall mechanical properties. Listed in Table 3, similar peptide amphiphile molecules that promotes cells adhesion (PA3) (see, e.g., Yamada, K. M., Journal of Biological Chemistry, 1991. 266(20): p. 12809-12812), accelerates bio-mineralization (PA4) (see, e.g., Veis, A., B. Sabsay, and B. W. Chou, Abstracts of Papers of the American Chemical Society, 1989. 197: p. 92-Taec; Hartgerink, J. D., E. Beniash, and S. I. Stupp, Science, 2001. 294(5547): p. 1684-1688), binds to bone morphogenetic protein (BMP) (PA5), have also been synthesized.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

---

We claim:

1. A composition comprising a bundle of a plurality of longitudinally aligned nanofibers, wherein said nanofibers comprise self-assembling peptide amphiphile molecules, wherein said self-assembling peptide amphiphile molecules comprise a hydrophobic tail, a peptide segment configured for beta-sheet formation, and a charged segment; wherein said self-assembling peptide amphiphile molecules interact to form aligned nanofibers; and wherein said bundle of aligned nanofibers comprises 15-35 nanofibers.

2. The composition of claim 1, wherein said hydrophobic tail comprises an alkyl tail.

3. The composition of claim 2, wherein said alkyl tail comprises at least 16 carbon atoms.

4. The composition of claim 1, wherein said peptide segment configured for beta-sheet formation comprises uncharged amino acid residues.

5. The composition of claim 4, wherein said peptide segment configured for beta-sheet formation comprises three alanine and three valine amino acid residues.

6. The composition of claim 1, wherein said charged segment comprises a charged peptide segment comprising charged amino acid residues.

7. The composition of claim 6, wherein said charged amino acid residues comprises three glutamic acid residues.

8. A bundle of longitudinally aligned nanofibers, wherein said nanofibers comprise self-assembling peptide amphiphile molecules, wherein said self-assembling peptide amphiphile molecules comprise a hydrophobic tail, a peptide segment and a charged segment; wherein said bundle of nanofibers comprises 15-35 nanofibers.

* * * * *

SEQUENCE LISTING

<160> NUMBER OF SEQ ID NOS: 11

<210> SEQ ID NO 1
<211> LENGTH: 40
<212> TYPE: DNA
<213> ORGANISM: Artificial Sequence
<220> FEATURE:
<223> OTHER INFORMATION: Synthetic

<400> SEQUENCE: 1
acctcgttga cacctggaag tcacgttgtt cctgttcagc                    40

<210> SEQ ID NO 2
<211> LENGTH: 47
<212> TYPE: DNA
<213> ORGANISM: Artificial Sequence
<220> FEATURE:
<223> OTHER INFORMATION: Synthetic

<400> SEQUENCE: 2
gtgatgtcct cgtctgtagc atcagtagac acatatgatg gccgagg             47

<210> SEQ ID NO 3
<211> LENGTH: 47
<212> TYPE: DNA
<213> ORGANISM: Artificial Sequence
<220> FEATURE:
<223> OTHER INFORMATION: Synthetic

<400> SEQUENCE: 3
tgtccacaaa gtcttcacct gtgtaggtga ggaccgtcta cgtgcat             47

```
<210> SEQ ID NO 4
<211> LENGTH: 41
<212> TYPE: DNA
<213> ORGANISM: Artificial Sequence
<220> FEATURE:
<223> OTHER INFORMATION: Synthetic

<400> SEQUENCE: 4
tggtgaaaga ggacggactg gaccagcagg accgacagga c                41

<210> SEQ ID NO 5
<211> LENGTH: 39
<212> TYPE: DNA
<213> ORGANISM: Artificial Sequence
<220> FEATURE:
<223> OTHER INFORMATION: Synthetic

<400> SEQUENCE: 5
agatggccct ggatgtggag ccctttgctc agggctggt                  39

<210> SEQ ID NO 6
<211> LENGTH: 42
<212> TYPE: DNA
<213> ORGANISM: Artificial Sequence
<220> FEATURE:
<223> OTHER INFORMATION: Synthetic

<400> SEQUENCE: 6
ctgtgcttcg tcacccacgt agatgctccc agggctgttt tc              42

<210> SEQ ID NO 7
<211> LENGTH: 9
<212> TYPE: PRT
<213> ORGANISM: Artificial Sequence
<220> FEATURE:
<223> OTHER INFORMATION: Synthetic

<400> SEQUENCE: 7

Val Val Val Ala Ala Ala Glu Glu Glu
1               5

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8

Val Val Val Ala Ala Ala Glu Glu Glu Gly Ile Lys Val Ala Val
1               5                   10                  15

<210> SEQ ID NO 9
<211> LENGTH: 14
<212> TYPE: PRT
<213> ORGANISM: Artificial Sequence
<220> FEATURE:
<223> OTHER INFORMATION: Synthetic

<400> SEQUENCE: 9

Val Val Val Ala Ala Ala Glu Glu Glu Gly Arg Gly Asp Ser
1               5                   10

<210> SEQ ID NO 10
<211> LENGTH: 13
<212> TYPE: PRT
<213> ORGANISM: Artificial Sequence
```

```
<220> FEATURE:
<223> OTHER INFORMATION: Synthetic

<400> SEQUENCE: 10

Val Val Val Ala Ala Ala Glu Glu Glu Gly Ser Pro Gly
1               5                   10

<210> SEQ ID NO 11
<211> LENGTH: 21
<212> TYPE: PRT
<213> ORGANISM: Artificial Sequence
<220> FEATURE:
<223> OTHER INFORMATION: Synthetic

<400> SEQUENCE: 11

Val Val Val Ala Ala Ala Glu Glu Glu Ser Gly Gly Gly Tyr Tyr Pro
1               5                   10                  15

Val His Pro Ser Thr
            20
```